United States Patent [19]

Jacobson et al.

[11] 4,339,163

[45] Jul. 13, 1982

[54] BAG-LIKE CONTAMINANT CONTROL WORK MODULE

[75] Inventors: Earl B. Jacobson, Crystal Lake, Ill.; H. F. Buchanan, Port St. Lucie, Fla.

[73] Assignee: Nuclear Power Outfitters, Crystal Lake, Ill.

[21] Appl. No.: 137,124

[22] Filed: Apr. 4, 1980

[51] Int. Cl.[3] ........................ A61B 19/00; G21C 11/00

[52] U.S. Cl. ........................................ 312/1; 128/1 R; 250/515

[58] Field of Search ........................... 312/1; 128/1 R; 250/515

[56] References Cited

U.S. PATENT DOCUMENTS

| | | | |
|---|---|---|---|
| 3,115,450 | 12/1963 | Schanz | 250/515 |
| 3,355,230 | 11/1967 | Trexler | 312/1 |
| 3,576,206 | 4/1971 | Trexler | 312/1 |
| 3,670,718 | 6/1972 | Brendgord | 312/1 |
| 3,713,480 | 1/1973 | Low et al. | 312/1 |
| 3,744,055 | 7/1973 | Brendgord | 312/1 |
| 3,802,416 | 4/1974 | Cazalis | 128/1 R |
| 3,850,172 | 11/1974 | Cazalis | 128/1 R |

*Primary Examiner*—Victor N. Sakran

*Attorney, Agent, or Firm*—Winburn & Gray, Ltd.

[57] ABSTRACT

A bag-like contaminant control work module formed from a flexible impervious membrane which is inflated inside of an enclosed workspace to protect workers in the module from contaminants. The workspace, such as in a nuclear power steam generator, has a portal or manway opening into the workspace into which the module is secured by a module passageway. The module includes one or more glove boxes, in which the workers perform their assigned tasks after passing through the passageway and portal. The module includes one or more absolute filters allowing passage of air flow through the module passageway and into the workspace only through the filters. The module may include an auxiliary passageway secured to the outside of the module passageway and also secured in the portal opening and through which items can be passed back and forth to the worker in the glove box from outside the portal. The module is invertible so that it can be pulled out of the workspace trapping all the contaminants therein and disposed of without handling the contaminants.

9 Claims, 8 Drawing Figures

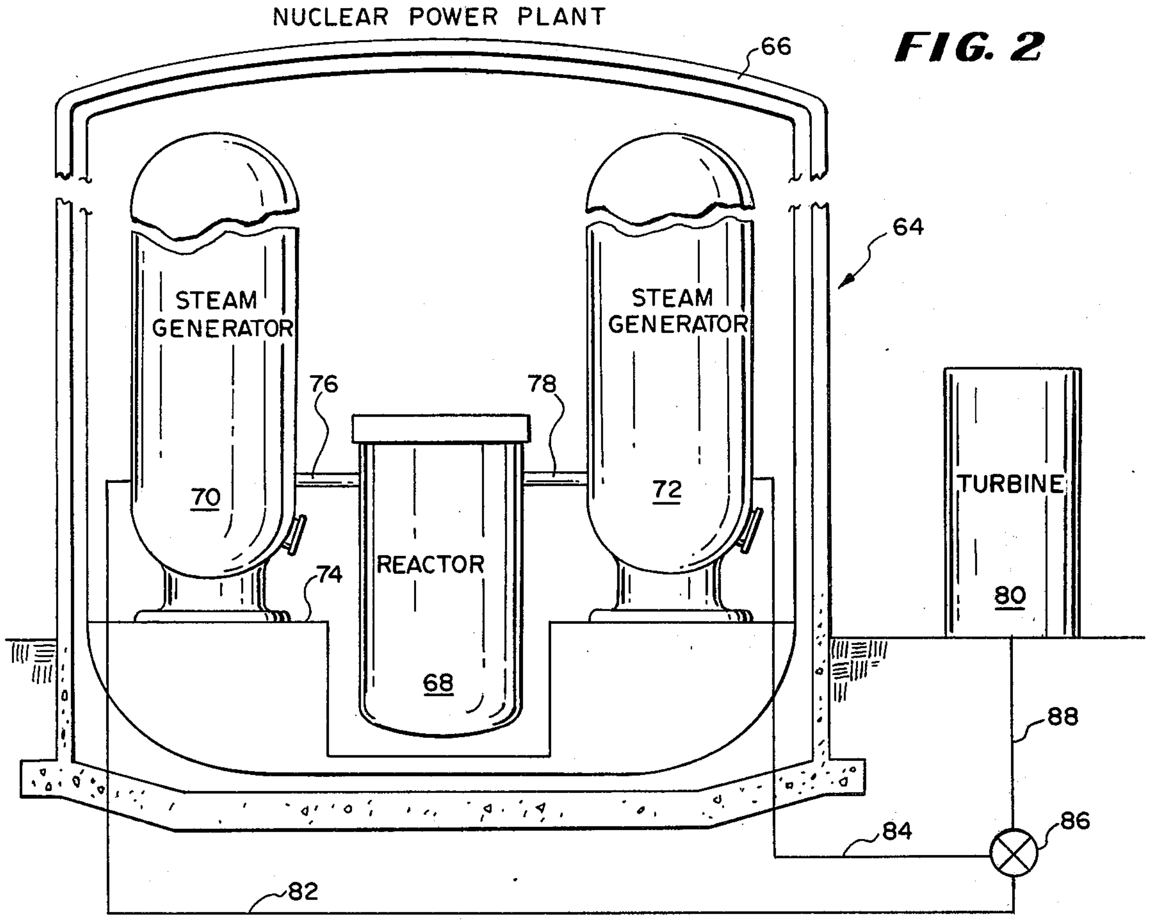
FIG. 2
FIG. 8
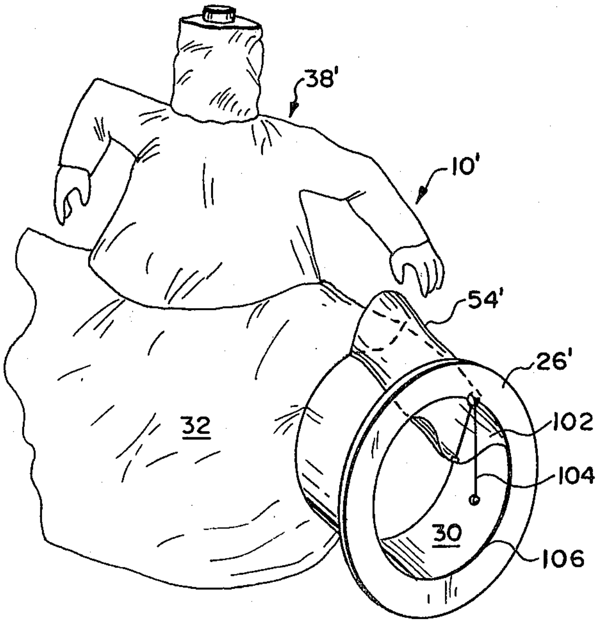

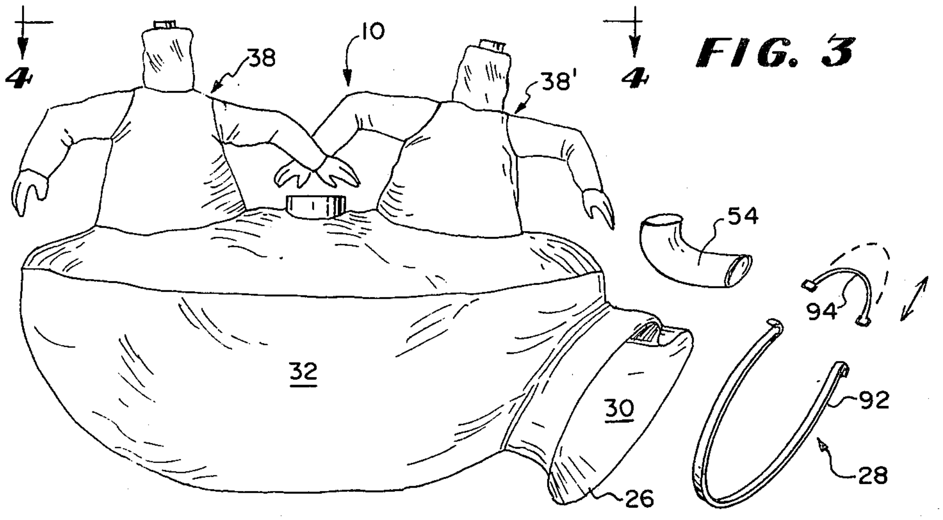
FIG. 3
FIG. 4
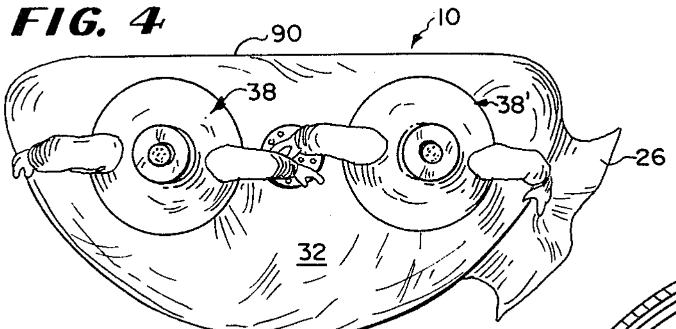
FIG. 5
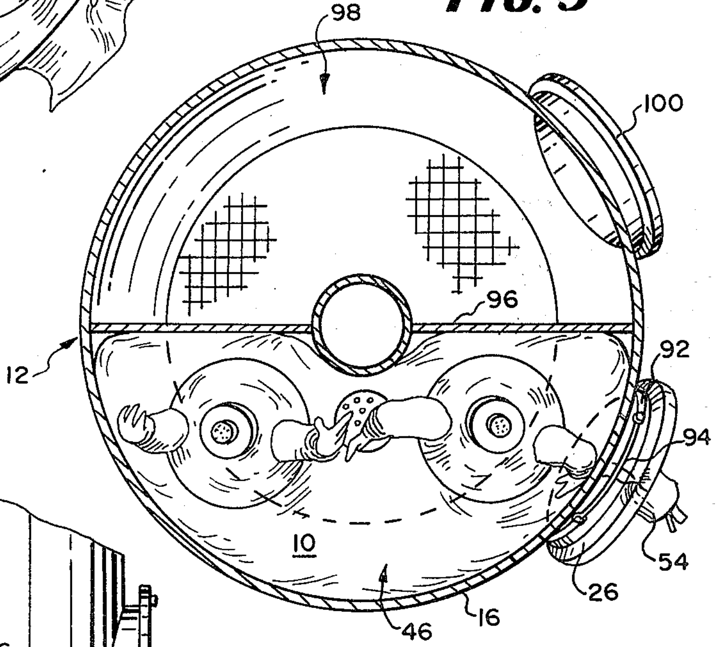
FIG. 6
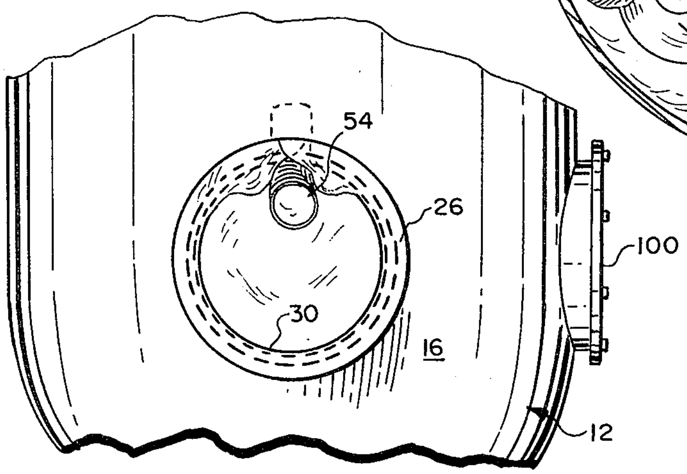
FIG. 7
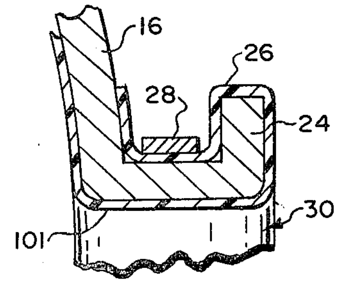

BAG-LIKE CONTAMINANT CONTROL WORK MODULE

BACKGROUND OF THE INVENTION

The invention relates generally to contaminant control systems and more particularly to a bag-like work module which enables workers to work in an enclosed workspace without physical contact with contaminants in the workspace.

In nuclear power plants, steam generators typically are utilized as heat exchangers between the reactor and a power generating steam turbine. The steam generators have hundreds or thousands of heat exchange tubes in single pass or double pass loop tubes inside the generator housing. The tubes carry uncontaminated water through the generators which is converted into steam to drive the turbine by hot water from the reactor flowing around the outside of the heat exchange tubes. Periodically, typically during a reactor refueling outage, or if a leak occurs, the tubes are checked to make sure they are not leaking or stressing to the point where they will leak.

The tubes are checked by running a tester, typically an eddy current tester, over the length of each tube to be checked. Typically, unless a leak has occurred, some predetermined number of the thousands of tubes are checked during each outage so that during a period of time all the tubes are checked. The testers are operated, repairs or sealing off of leaking tubes are performed by workers physically climbing into the steam generators through a manway or portal in the generator housing. The interior of the generators, which typically are sixty feet high, is full of contaminants from the reactor water which are on the interior surfaces of the housing and are dislodged by the workers themselves from the tubes and surfaces. This causes surface contamination of the worker's garments, which contamination is then brought out of the generator when the workers climb out of the portal.

Further complicating the problem, is the fact that the interior or workspace of the generator is radioactive and the workers are only permitted to be inside the generator for a few minutes at a time. The checking and repairs may require hundreds of entrances and exits during a refueling outage of eight weeks. The generators typically are worked on for two weeks out of an eight week refueling outage.

Each worker typically is attired in several layers of clothing covered by a plastic outer layer and a self contained breathing apparatus. This makes it difficult to pass through the portals, which usually are small on the order of sixteen inches in diameter, and the clothing itself is cumbersome to work in.

Further, each time the worker leaves the generator at least the outer clothing which has radioactive contaminants on it has to be removed and disposed of. The area around the portal becomes contaminated and must be cleaned. The workers outside the generator are exposed to the contaminants brought out on the clothing and the worker himself is further exposed because the contaminants are in physical contact with the clothing and remain there while the clothing is further handled and disposed of.

The invention permits workers to work in a cool, comfortable environment without cumbersome extra clothing and air masks. The workers pass into and out of the module of the invention without physical exposure to the contaminants and without carrying contaminants outside the workspace. Thus, the length of exposure to the workers is reduced, the amount of material to be disposed of is greatly reduced and contamination of workers and outside areas are substantially eliminated. Further, the contaminants are not handled when the job is finished because the module is inverted and disposed of with the contaminants enclosed therein.

SUMMARY OF THE INVENTION

The above and other disadvantages of prior art contaminant control techniques and systems are overcome in accordance with the present invention by providing a bag-like contaminant control work module which insulates the workers from physical contact with the contaminants, remains in place in the workspace until the work is completed and is inverted and collapsed within itself when the work is completed to trap all the contaminants therein for disposal without further handling or contamination of the area outside the workspace. The module is formed from a flexible impervious membrane which is inflated inside the workspace through a worker passageway into the module and workspace. The module has one or more filters which pass air only through the module into the workspace. At least one glove box is formed in the membrane to provide a work area for the worker therein.

BRIEF DESCRIPTION OF THE DRAWINGS

FIG. 2 is a partial block and diagrammatic view of a nuclear power plant;

FIG. 3 is a perspective view of the inflated work module with an exploded view of one securing means and auxiliary passageway;

FIG. 4 is a top plan view of the work module of FIG. 3 taken along the line 4—4 therein;

FIG. 5 is a top sectional view of the work module in the generator of FIG. 1 taken along the line 5—5 therein;

FIG. 6 is a front plan view of the steam generator portal of FIG. 1 with the work module therein taken along line 6—6 therein;

FIG. 7 is a partial sectional view of one edge of the generator portal of FIG. 1 with the work module secured therein taken along line 7—7 therein; and FIG. 8 is a partial perspective view of a second embodiment of auxiliary passageway.

DESCRIPTION OF THE PREFERRED EMBODIMENTS

Figure 1:
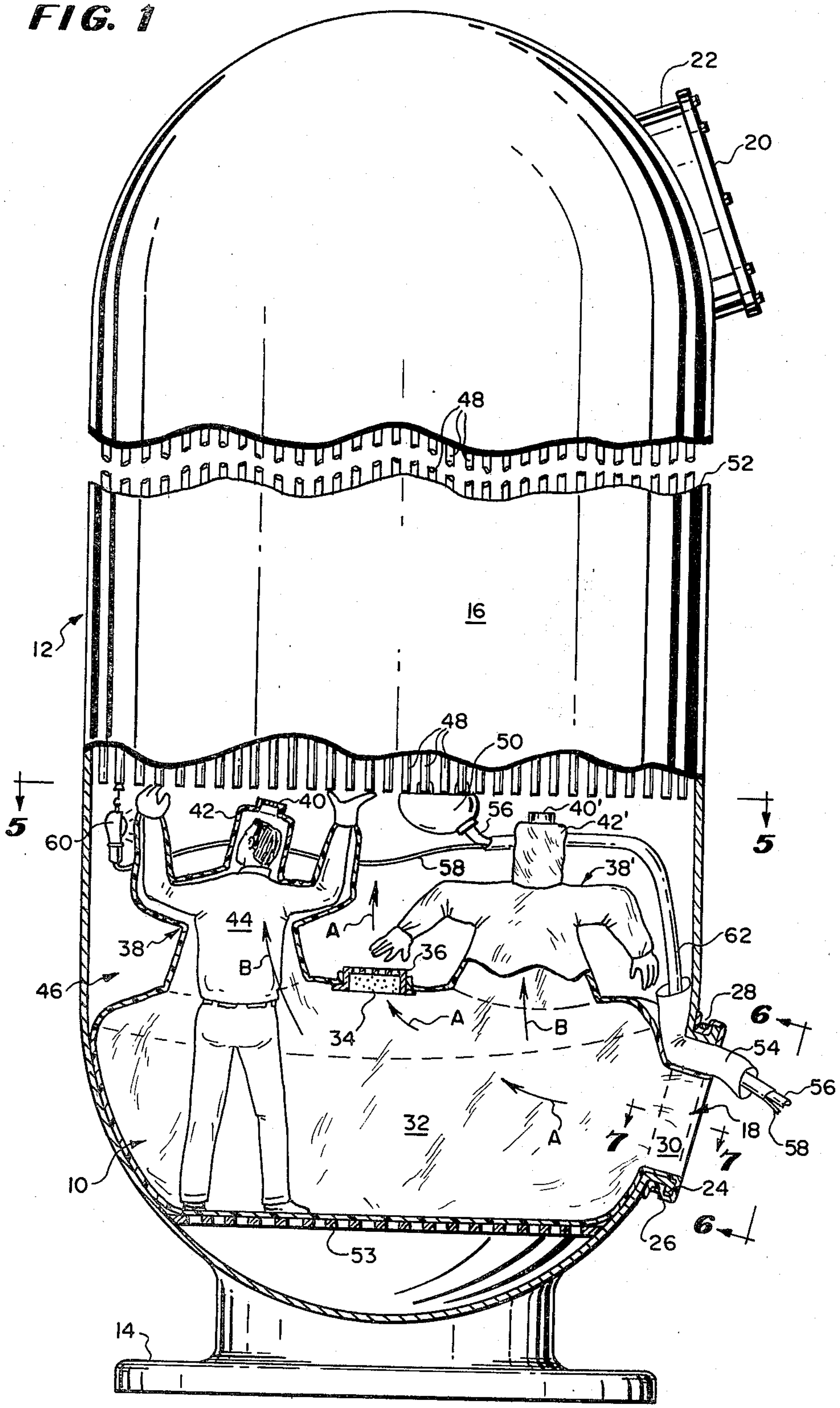
FIG. 1 is a side plan view with portions broken away of one embodiment of the work module of the invention in a steam generator.

Referring to FIG. 1, a work module embodying the invention is designated generally by the reference numeral 10. The bag-like work module 10 is shown operatively in place in a steam generator 12. The generator 12 includes a base 14 and an outer housing 16. The housing 16 includes a portal or manway 18. The portal 18 is sealed and secured by a plate, similar to a plate 20 covering an upper portal 22 when the generator is in operation.

The portal 18 includes a lip 24 around which is secured a flange 26 of the module 10. The flange 26 may be secured to the portal 18 in a number of ways, here illustrated by a securing band or belt 28 which is wrapped around the flange 26 behind the lip 24. The flange 26 is formed with or secured to a passageway 30 formed in the module 10. The module 10 is formed from a flexible impervious membrane material, such as a plastic coated nylon web, and is inflated by air flowing through the passageway 30 into a module body 32 and out of a filter 34 as shown by arrows "A". The air flow may be pumped into the passageway 30 or pumped out the top of the generator 12 through an opening or portal. (not shown)

The filter 34 is made of an absolute filter material in a plastic or other light weight bracket 36 sealed into one wall of the body 32. The body 32 also includes one or more glove boxes 38 sealed and secured to the body 32 or formed therewith. Each of the glove boxes 38 and 38' may also include an absolute filter 40 in a head piece 42 of the glove box to provide air flow through the head pieces as shown by arrows "B". Alternately, positive air flow tubes may be fitted into the head pieces 42, which air flow will then also flow out of the filter 34. The head pieces 42 and 42' are, at least partially, transparent so that a worker 44 may see therethrough to perform the necessary operations in the tube inspection and repair.

The module 10 is inserted through the portal 18 into a workspace 46 which is formed at one or both ends of the generator 12. The generator has thousands of heat transfer water tubes 48 extending the length thereof to exchange heat between the hot water from the nuclear reactor and the water in the tubes 48 which is turned to steam to run a power generating turbine. The tubes 48 may extend in loops to the top of the generator 10 and back to the bottom in which case the workspace 46 is in one half of the housing 16 (FIG. 5). A tube checker 50 will travel up each tube 48 to be checked and down to the other side and back. The tubes 48 may extend in one pass through the generator 10 in which case the workspace 46 will be the whole portion of each end of the housing 16. The housing 16 is shown broken away at 52, to indicate the generator is not drawn to scale, since the generator 10 would be on the order of sixty-two feet in length or height.

The module 10 is placed on a platform or grate 53 which is placed in the housing 16 after the portal 18 is opened. An auxiliary sleeve or passageway 54 is placed through the portal 18 on top of the passageway 30. The sleeve 54 may be secured to the outer upper portion of the passageway 30. The auxiliary sleeve 54 is used to pass power cables 56 and 58 and tools to the workspace 46. The power cable 56 provides power to the checker 50 and moves in and out of the sleeve 54 as the checker 50 moves up and down the tubes 48. The cable 58 provides power to a lamp 60 or other power tools. One or both of the cables 56 and 58 may be encased in a protective sleeve 62 which is made of a material to resist tearing and wear by the cable movement.

The flange 26 then is secured to the portal 18 by the band 28. The body 32 is inflated by the pressure differential through the filter 34 or filters 40. The worker 44, wearing loose fitting normal garments, then enters through the passageway 30. The worker or workers may climb in and out of the module 10 as desired without changing clothes or removing contaminants from the workspace 46, which contaminants are all contained on the outside of the module 10. If one of the tubes 48 is discovered to have a leak and cannot be repaired, a mechanical or explosive bolt is utilzed to seal off the tube.

Once the tube checking and other inspection and repair operations are completed, the worker 44 removes the module 10 through the portal 18 by pulling one of the glove boxes 38 or 38' or other portion of the body 32 to invert the module 10 upon itself. The inverted module 10 is pulled completely through the portal 18 trapping or containing all the contaminants inside the inverted module 10. The module flange 26 is unfastened from the portal lip 24 and secured to close off the passageway 30, following which the module 10 and contaminants are disposed of without handling the contaminants or contaminating the area outside the portal 18.

Referring now to FIG. 2, a typical nuclear power plant 64 includes a main building 66 in which are housed a reactor 68 and a pair of steam generators 70 and 72. The reactor 68 and generators 70 and 72 are installed in a floor 74. The reactor 68 is coupled to each generator 70 and 72 and their tubes 48 by respective lines 76 and 78. Each of the generators 70 and 72 is coupled to a power generating turbine 80 by lines 82 and 84 coupled through a valve 86 to a line 88. Thus, during each outage, at least two modules 10, one for each generator 70 and 72 will be utilized in each power plant. The two modules 10 replace numerous items of individual clothing for the workers who are very limited in the amount of time they can spend in the generator and which work may be taking place for two weeks of an eight week refueling outage. The lines shown with the plant 64 are merely for illustration and in reality there may be numerous other interconnecting and return lines between the various elements.

One module 10 for a half workspace 46, is illustrated inflated outside the workspace in FIGS. 3 and 4. The module 32 is shaped to fit into the workspace 46 and has a substantially flat wall 90. The module membrane is very flexible and the workers can move around easily in the glove boxes 38 and 38'. The auxiliary sleeve 54 is a separate sleeve in this embodiment. The securing band 28 includes two spring pieces 92 and 94 which engage over the ends of one another when the flange 26 is folded back over the portal lip 24. The band 28 also may be an adjustable strap (not illustrated).

The module 10 secured in the workspace 46 is illustrated in FIGS. 5 and 6. The workspace 46 is defined by a septum 96. The loop tubes 48 start on one side of the septum 96 and return on the other side of the septum. A space 98 on the opposite side of the septum 96 may be reached by a separate portal 100. The auxiliary sleeve 54 is positioned at the top of the passageway 30 to provide as small an obstruction to the passage of the workers therethrough as possible.

An inner spring band 101 (FIG. 7) may be utilized to keep the passageway 30 as open as possible. The band 101 may be sized to fit across the width of the portal 18 and may terminate on either side of the sleeve 54 or may include a flexible portion or separate flexible or formed piece (not illustrated) to keep the sleeve 54 as close to the wall of the portal as possible.

Referring to FIG. 8, a second module embodiment 10' having an auxiliary sleeve 54' and module flange 26' is illustrated. The sleeve 54' is similar to the sleeve 54 being of a diameter to accommodate the lines and passage of tools therethrough and of a length having an opening 102 outside the portal 18 and opening into the workspace 46 on the other end. The sleeve 54' is sewn to the outside of the passageway 30 which is formed without the flange 26. The sleeve 54' has a drawstring 104 secured beneath it adjacent the passageway 30 and passing across it and out the top thereof. The module flange 26' is then sewn and sealed along a seam 106 around the opening of the passageway 30 and the opening 102 of the sleeve 54. The drawstring 104 passes through or adjacent the seam 106. When the module flange 26' is secured around the portal 18, the drawings 104 may be pulled tight to allow workers to pass in and out of the passageway 30 with maximum clearance.

Many modifications and variations of the present invention are possible in light of the above teachings. The drawings are not drawn to scale, for example, the sixteen inch diameter portal 18 would be smaller than that shown in FIG. 1 relative to the worker 44. The upper portion of the body 32 and the glove boxes 38 and 38' may be a plastic film material for flexibility. The main portion of the body 32 and module 10 may be made of 10 to 28 ounce per yard plastic coated or plastic laminated nylon or polyester. The heavier 28 ounce material may be used for the bottom of the body 32 to provide extra strength for the worker 44 to walk on. It is, therefore, to be understood that within the scope of the appended claims, the invention may be practiced otherwise than as specifically described.

What is claimed and desired to be secured by Letters Patent of the United States is:

1. A contaminant control work module comprising:

bag-like flexible membrane means having a first passageway in said membrane means of a size to permit passage of a worker therethrough and a shape and size adapted, when inflated by a pressure differential, to substantially enclose at least one worker therein;

filter means in said membrane means to allow air flow through said membrane means only in one direction from said passageway through said membrane means;

at least one glove box means in said membrane means having a head piece, said head piece having substantially transparent portions therein and a pair of glove fitted arm extensions adapted for a worker to fit therein to work in said membrane means shielded from outside contaminants;

each said head piece including separate filter means therein to provide air flow through each said glove box means only in one direction from said passageway through said membrane means;

said membrane means are adapted to be placed in a substantially enclosed contaminant containing workspace through workway portal means opening into said workspace, said workspace having a predetermined configuration and being defined by an upper and lower portion therein, said membrane means when inflated substantially filling said lower portion of said workspace and allowing said glove box means to be moved about said upper portion;

said first passageway having means adapted to be secured around said portal means to secure said membrane means in said workspace while allowing workers to pass through said first passageway;

said workspace is in a radioactive environment; and said membrane means are collapsible and invertible to contain contaminants in contract with the other surface thereon when said membrane means are removed from said workspace and disposed of.

2. The work module of claim 1 wherein:

said workspace is a nuclear power plant steam generator.

3. The work module of claim 1 wherein:

said membrane means include at least two glove box means therein.

4. The work module of claim 1 wherein:

said first passageway includes an external opening and said means to be secured are flange means around said opening adapted to overlap and be secured around said portal means.

5. The work module of claim 1 wherein:

said membrane means include an auxiliary passageway secured to said first passageway and adapted to be secured through said workway portal means to allow passage of items between said glove box means inside said workspace and to an area external to said workspace and portal means.

6. The work module of claim 5 wherein:

said first and auxiliary passageways include an external opening and said means to be secured are flange means connected around said openings having both openings inside said flange means and adapted to overlap and be secured around said portal means.

7. The work module of claim 6 wherein:

said auxiliary passageway includes means to substantially collapse said auxiliary passageway opening.

8. The work module of claim 1 wherein:

said flexible membrane means are formed at least in part by one of plastic coated or plastic laminated nylon.

9. The work module of claim 1 wherein:

said flexible membrane means are formed at least in part by one of plastic coated or plastic laminated polyester.

* * * * *